United States Patent [19]

Greenfield et al.

[11] 3,980,436

[45] Sept. 14, 1976

[54] ANALYTIC TEST DEVICE

[75] Inventors: Walter Greenfield, Ardsley; Raymond Berg, Scarsdale, both of N.Y.

[73] Assignee: Sci-Med Laboratories, Inc., Hartsdale, N.Y.

[22] Filed: Dec. 19, 1974

[21] Appl. No.: 534,476

[52] U.S. Cl. .......................... 23/253 R; 23/253 TP; 23/259; 128/2 F

[51] Int. Cl.[2] .................... G01N 31/22; G01N 1/10; A61B 1/10

[58] Field of Search ........... 23/259, 253 TP, 253 R, 23/292; 128/2 F, 295; 73/421 R

[56] References Cited

UNITED STATES PATENTS

| | | | |
|---|---|---|---|
| 2,643,940 | 6/1953 | Stevens | 23/259 |
| 2,667,075 | 1/1954 | Blum et al. | 23/259 X |
| 3,705,012 | 12/1972 | Marmor et al. | 23/259 X |
| 3,774,455 | 11/1973 | Seidler et al. | 23/259 X |

*Primary Examiner*—Norman Yudkoff
*Assistant Examiner*—Barry I. Hollander
*Attorney, Agent, or Firm*—Fidelman, Wolffe & Waldron

[57] ABSTRACT

An analytic test device of a one time use type formed by concentrically disposed tube and sleeve members. A test reagent is present in the annular region between tube and sleeve. A liquid sample placed inside the tube is unable to enter the reagent containing annular region until relative movement between tube and sleeve opens a passage for sample flow into the annular region and contact with the test reagent.

The test device is particularly adapted to testing urine samples.

6 Claims, 6 Drawing Figures

ANALYTIC TEST DEVICE

BACKGROUND OF THE INVENTION

In a common laboratory testing system for medical purposes, the laboratory technician dips chemically impregnated paper strips into the sample or specimen (e.g. of urine) and observes a color change in the strip, the change depending on the composition of the strip impregnant and the biochemical reactions involved. Laboratory analyses are very quickly and easily conducted with the strips.

Notwithstanding simplicity (at least insofar as the technician is concerned), closer control of the test is desirable, including, for example, a limit on the quantity of urine in contact with the strip. It has now been found possible to construct a collecting and testing unit that greatly facilitates conduct of the analytical test and reduces chances for contamination and mistakes.

SUMMARY OF THE INVENTION

Briefly stated, the present invention involves an integrated sample collection and testing unit formed from two concentric tubular components. One component constitutes a sample chamber hereinafter called the tube, and the other component is a sleeve member open top and bottom and sized to concentrically interfit internally or externally with the first component, i.e. the tube. The tube-sleeve structure provides an annular region between adjacent tube and sleeve side walls. This annular region can be sealed off from the sample or opened to the sample as desired without leaking sample from the assembled testing unit.

The tube or sleeve wall surface facing the annular region is provided with one or more recesses, in which can be placed analytical test reagents. Paper strips impregnated with the analytic test reagents are a convenient and preferred reagent insert.

Means are provided to seal the annular region against sample flow thereinto, such means normally being a fluid tight sealing structure. However, the sealing means may constitute an interfit between tube and sleeve tight enough to avoid leakage. However, an important aspect of this invention is that tube and sleeve are relatively movable, so that the tube and sleeve interfit may be shifted as desired from a fluid tight sealed position to an open position wherein sample flows into the annular region. In the open position a controlled amount of sample flows into the annular region, wets the test reagent to cause the test reaction. Forming the outer component from a transparent material allows the test results to be seen by the technician, or be measured by an optical instrument.

DETAILED DESCRIPTION OF THE INVENTION

For further understanding of the present invention, reference is now made to the attached drawings, wherein a preferred embodiment of test unit is illustrated. In the drawing.

Figure 1:
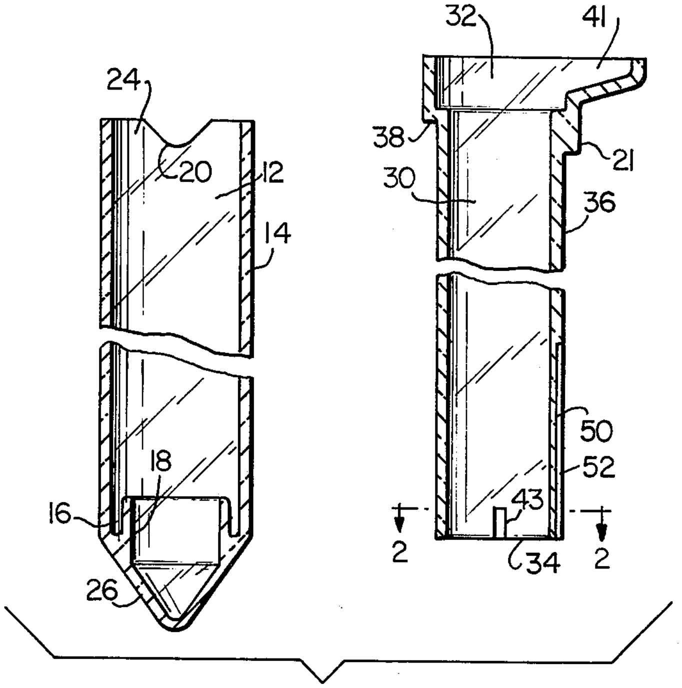
FIG. 1 is a cross-section through the tube and sleeve components in an unassembled state.
Figure 3:
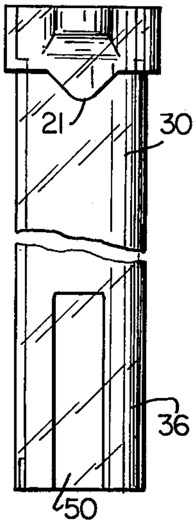
FIG. 3 is a side view of the sleeve.

As may be seen in FIG. 1, the tube or sample container 12 is the outer component and is formed with an imperforate side wall 14, open top rim 24 and a sealed bottom well 26, all of which makes tube 12 suitable for liquid sample retaining purposes. Just above bottom well 26 is a U-shaped channel 16 sized and shaped for close interfit of a cylindrical sleeve against the inner channel wall 18. At the top 24, the side wall 14 contains a gently curved slot 20. It may be noted that tube 12 has a structure capable of being formed by plastic molding techniques in large numbers relatively inexpensively.

Also shown in FIG. 1 is a sleeve 30, adapted to interfit with container tube 12 to form a complete sample collecting vessel and test device. To this effect, sleeve 30 is formed with open top 32 and open bottom 34 and with an imperforate side wall 36 sized for a concentric relationship with the inside surface of side wall 14 on container tube 12. Sleeve 30 is formed with an annular shoulder 38 thereon which seats on the top rim 24 of container tube 12. The sleeve 30 is supported by rim 24.

Figure 5:
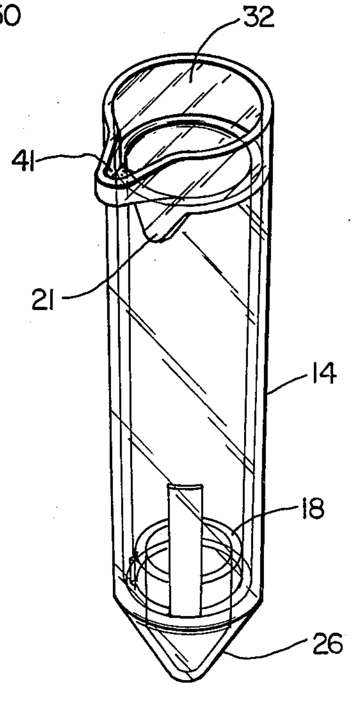
FIG. 5 is a pictorial view of the test unit.

The side wall of sleeve 30 near the bottom 34 thereof may be tapered and bevelled to ensure entry into channel 16 and to bear against channel wall 18. Normally sleeve bottom 34 is clear of the bottom of channel 16. Consequently, the assembled tube 12 and sleeve 30 interfit to form the test device 10 shown in FIG. 5 with container tube 12 and sleeve 30 having a watertight but relatively rotatable relationship.

For user convenience the top of sleeve 30 is formed with a pouring lip 41.

In the preferred embodiment illustrated in the drawing, cooperating means are provided to facilitate assembling the test device 10 locked into the sealed position. Allusion has already been made to the slot 20. A cam 21 (which conveniently may be formed under pouring lip 41) extends down as an extension of shoulder 38, with cam 21 being in slot 20 in the sealed position.

Figure 4:
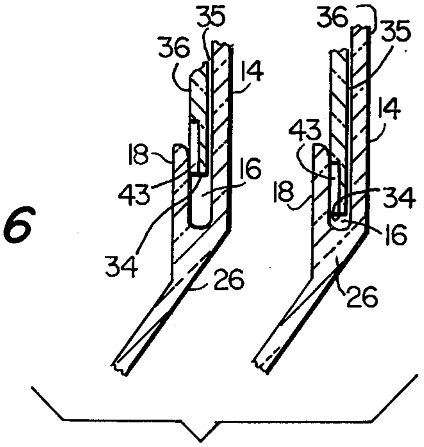
FIG. 4 is a partial cross-section illustrating the sealing fit of the test unit.
Figure 2:
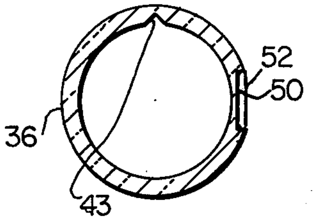
FIG. 2 is a section taken along line 2—2 of FIG. 1.

The side wall 36 of sleeve 30 has a V-shaped notch 43 formed on the inside surface at the bottom of the sleeve. The notch 43, which may be rather short (e.g. 0.250 inch) is related to the depth of slot 20. When cam 21 is in slot 20, and sleeve 30 seats on the rim of tube 12, notch 43 is completely recessed inside channel 16 with an un-notched portion of the inside wall surface of side wall (above notch 43) bearing against channel wall 18 sealing the annular region 35 against sample leakage, as is shown in FIG. 4.

However, when tube 12 and sleeve 30 are rotated relative to each other, e.g. 90°, cam 21 rides up out of slot 20 onto the rim 24 forcing a longitudinal displacement of tube and sleeve which lifts the bottom 34 of sleeve 30 up inside channel 16. The V-notch 43 is no longer concealed behind channel wall 18, as is illustrated in FIG. 4. The longitudinal displacement has shifted test device 10 to an open position. Sample liquid flows down through notch 43 into the bottom of channel 16 then up into annular region 35, wetting a test reagent 52 disposed in a recess 50, which recess is conveniently formed in the outside surface of sleeve wall 36.

Since the interfit of tube 12 and sleeve 30 provides relatively little volume for any liquid in annular region 35, capillary action helps to create liquid sample migration into region 35, but only a limited volume of liquid can transport to react with test reagent 52. If strict volume control is desired and back diffusion of reactants prevented, test device 10 can be shifted back to the closed position by relative rotation back to the closed position after the test reagent 52 is adequately wetted.

It may be noted that sleeve 30 has a structure capable of being formed by plastic molding techniques in large numbers and relatively inexpensively. Recess 50 and notch 43 extend to the bottom 34 of the sleeve, which facilitates fabrication, and for that matter insertion of a reagent containing test strip 52 into recess 50.

In any event the test reagent 52 (desirably in strip form) is placed into recess 50, then the reagent containing sleeve 30 is inserted into tube 12 with tube and sleeve disposed in the closed or sealed position. The sealed position is normally employed for packaging of test unit 10 and shipping. Test reagent 52 is protected by the sealed character of the sealed position. If desired, a stopper (not shown) may be included in the package so that the open mouth 32 of test unit 10 can be closed (after sample has been placed inside) to prevent odor or spillage.

To analyze the sample placed inside test unit 10, the user rotates the container 12 and sleeve 30 relative to one another, e.g. 90° to the open position. The (urine) sample flows through notch 43 to the recess 50 and there contacts the reagent strip 52. Thereafter the user rotates or back rotates container 12 until the closed position is reached. To the extent that the opened position illustrated in FIG. 4 can be considered the active position, a subsequent closed relationship as also is shown in FIG. 4 constitutes a deactivated position which prevents the sample urine from further contact with the test reagents (if further contact is not desired).

Analytic tests of the nature contemplated for use with the test device of the present invention usually involve color change; the nature of the color change constitutes the test result. Accordingly, once sleeve and tube have been rotated to the deactivated or closed position, the technician is free to observe the color change of the reagents through the transparent side wall 14 of tube 12. After the user has interpreted, recorded, etc. the test results, the test device 10 with sample therein is still available for further use, e.g. as a centrifuge tube for measuring sediment, etc.

Once used, the test device 10 may be discarded. The one time use concepts embodied in the illustrated test device of the present invention are advantageous. Spillage, odor, and the unpleasant handling characteristics of prior art test systems can be avoided by one time use of this test device.

The materials involved in the test device of the present invention form no part of the invention and the actual analytic tests are known to the prior art. Tube 12 and sleeve 30 should be transparent components and for example, may be plastic materials such as polyethylene, polycarbonates, and the like, injection molded into the desired shape. The reagent can of course be inserted as part of the assembly of sleeve 30 and tube 12. Test reagents impregnated on paper or paper like materials supports can be obtained commercially. Such pre-prepared strips may be cut to size and placed into the recess or recesses 50 of sleeve 30.

Figure 6:
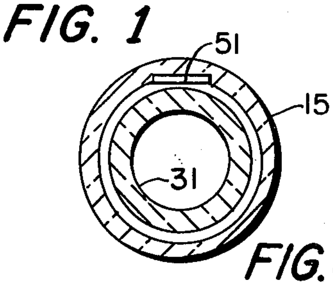
FIG. 6 is a cross-section of a different mode of tube and sleeve.

It should be appreciated that the structure illustrated by the drawing represents but a single, although preferred, embodiment of this invention. The recess 50 may of course be placed in the tube wall rather than in the sleeve wall, as is illustrated in FIG. 6 wherein recess 51 is present in the wall of tube 15 rather than in sleeve

31. Also, the tube and sleeve concept may be embodied by an external sleeve and internal tube. Still other modes are contemplated. Thus, a liquid-tight fit between tube and sleeve can be employed with window apertures in the inside component wall alignable through rotation and/or longitudinal displacement into reagent containing recesses in the outside component wall. In short, considerable structural variations are contemplated as being encompassed within the scope of this invention and of the hereto appended claims.

What is claimed:

1. An analytic test device and receptacle for a liquid test sample which comprises:

a closely adjacent concentric tube and sleeve relatively movable one to the other, the concentric fit of tube and sleeve providing an annular region therebetween, the sleeve constituting the inner member and being adapted to contain a liquid sample therein;

a recess in the tube or sleeve wall surface bounding said annular region, said recess containing a test reagent therein;

sealing means provided on the tube for retaining the bottom rim of said sleeve in a fluid-tight seal against sample liquid migration under said rim into said annular region, the seal of said sealing means being opened by relative movement of tube and sleeve whereby sample liquid helped by capillary action migrates into said annular region and into contact with test reagent.

2. The analytic test device of claim 1 wherein the tube and sleeve are transparent whereby color change in the test reagent is visible.

3. An analytic test device and receptacle for a liquid test sample which comprises:

a closely adjacent concentric tube and sleeve relatively movable one to the other, the concentric fit of tube and sleeve providing an annular region therebetween and said sleeve being an internal member adapted to contain a liquid sample therein;

a recess in the sleeve wall surface facing said annular region, said recess containing a test reagent therein;

sealing means at the juncture of the sleeve bottom and said tube for preventing liquid sample from migrating past the sleeve bottom into said annular region; and a liquid passage means at the sleeve bottom, opened by relative movement of tube and sleeve whereby sample liquid helped by capillary action migrates through said liquid passage means into said annular region and into contact with the test reagent.

4. The analytic test device of claim 3 wherein a U-shaped channel in said tube adjacent the bottom thereof receives the sleeve bottom and acts as the sealing means.

5. The analytic test device of claim 4 wherein said sleeve extends longitudinally beyond said tube and seats upon an open rim top surface of said tube and wherein the sleeve bottom seals against the channel wall.

6. The analytic test device of claim 4 wherein a notch at the sleeve bottom constitutes the liquid passage means, said notch being sealed off in the U-shaped channel until longitudinal relative movement of sleeve and tube raises said notch out of the U-shaped channel.

* * * * *